United States Patent [19]

Hennig et al.

[11] Patent Number: 5,434,305
[45] Date of Patent: Jul. 18, 1995

[54] PROCESS FOR THE PRODUCTION OF AROMATIC CARBODIIMIDES

[75] Inventors: Hans-Joachim Hennig, Leverkusen, Germany; Wolfgang Alter, Milan, Italy; Jörg Lüssmann, Dormagen, Germany

[73] Assignee: Rhein Chemie Rheinau GmbH, Mannheim, Germany

[21] Appl. No.: 165,425

[22] Filed: Dec. 6, 1993

[30] Foreign Application Priority Data

Dec. 16, 1992 [DE] Germany ............... 42 42 504.2

[51] Int. Cl.$^6$ ............................................. C07C 239/02
[52] U.S. Cl. ................................................ 564/252
[58] Field of Search ................................... 564/252

[56] References Cited

U.S. PATENT DOCUMENTS

| | | | |
|---|---|---|---|
| 2,853,473 | 9/1958 | Campbell et al. | 260/77.5 |
| 2,853,518 | 9/1958 | Balon et al. | 260/551 |
| 3,267,137 | 8/1966 | Fischer et al. | 260/551 |
| 3,502,722 | 3/1970 | Neumann | 260/566 |
| 3,635,947 | 1/1972 | Kober et al. | 260/239 |
| 3,644,456 | 2/1979 | Ulrich | 560/35 |
| 4,096,334 | 6/1978 | Keil | 560/35 |
| 4,260,554 | 4/1981 | Ohlinger et al. | 560/331 |

FOREIGN PATENT DOCUMENTS 2556760 6/1977 Germany .
2837770 3/1980 Germany .

*Primary Examiner*—Peter O'Sullivan
*Assistant Examiner*—Brian M. Burn
*Attorney, Agent, or Firm*—Connolly & Hutz

[57] ABSTRACT

A process for the production of aromatic carbodiimides by carbodiimidization of aromatic monoisocyanates in the presence of distillable organic phosphorus compounds as catalyst at 120° to 220° C. up to a maximum degree of carbodiimidization of 80% and subsequent removal by distillation of the unreacted starting isocyanate together with the catalyst from the reaction mixture, optionally together with subsequent preparation by distillation, together with the carbodiimides obtainable in accordance with this process.

6 Claims, No Drawings

PROCESS FOR THE PRODUCTION OF AROMATIC CARBODIIMIDES

The invention relates to a novel process for the production of aromatic carbodiimides by the carbodiimidisation of aromatic monoisocyanates using distillable organic phosphorus compounds as dimerisation catalysts with complete removal of these catalysts from the product of the process by arresting the carbodiimidisation reaction at a maximum degree of carbodiimidisation of 80% and removing the catalyst together with unreacted starting isocyanate from the reaction mixture by distillation.

The production of carbodiimides by carbodiimidisation of aromatic monoisocyanates in the presence of organic phosphorus compounds as catalysts has long been known (c.f. for example U.S. Pat. No. 2,853,473 or U.S. Pat. No. 2,853,518). In the production of monocarbodiimides according to these prior publications, the reaction conditions leading to carbodiimidisation are generally maintained until the starting isocyanates used have been completely converted into carbodiimides, whereupon the reaction products are further prepared by distillation.

U.S. Pat. No. 3,502,722 describes inter alia the carbodiimidisation of 2- and/or 6-alkyl substituted, i.e. sterically hindered, phenyl isocyanates using the most varied carbodiimidisation catalysts, which are, however, generally clearly inferior in terms of their catalytic activity to the organic phosphorus compounds from the above-stated prior publications. The phospholines and in particular the phospholine oxides, of which 1-methyl-1-oxo-phospholene is particularly preferred, constitute particularly effective carbodiimidisation catalysts enabling the smooth carbodiimidisation of the starting isocyanate without by-products. The disadvantage of previously known processes using these catalysts was, however, that it was not possible to produce catalyst-free carbodiimides since it was impossible to separate the product of the process by distillation from the catalysts which are used in low concentrations. Moreover, aromatic carbodiimides are used as antioxidants for polyurethane and polyester/polyurethane plastics, an application demanding a high degree of purity of the aromatic carbodiimides and thus, if the stated phosphorus compounds are used as catalyst, the thorough removal of these compounds from the carbodiimide.

The object of the invention was therefore to provide a novel process for the production aromatic carbodiimides by carbodiimidisation of aromatic monoisocyanates using the preferred prior art phosphorus compounds as catalyst, which process enables the practically complete removal of the catalyst used from the product of the process by means of a simple measure.

This object could be achieved by the provision of the process according to the invention, which is described in greater detail below.

The present invention provides a process for the production of aromatic carbodiimides by carbodiimidisation of aromatic monoisocyanates in the presence of distillable organic phosphorus compounds which accelerate the carbodiimidisation of isocyanates with the elimination of carbon dioxide as catalysts at 120° to 220° C., characterised in that, at a degree of carbodiimidisation of the monoisocyanates used as starting material of a maximum of 80%, the as yet unreacted starting isocyanate is removed from the reaction mixture by distillation together with the catalyst and the carbodiimide is isolated as the distillation residue of this distillation.

Starting materials for the process according to the invention are any distillable monoisocyanates with aromatically bonded isocyanate groups. Phenyl isocyanates which are alkyl-substituted in the 2- and/or 6-position in relation to the isocyanate group and optionally additionally bearing other substituents, which phenyl isocyanates are of the type stated in U.S. Pat. No. 3,502,722, column 2, line 55 - column 3, line 15, wherein 2,6-diisopropylphenyl isocyanate is also the particularly preferred starting material according to the invention.

The catalysts used in the process according to the invention are distillable organic phosphorus compounds which accelerate the carbodiimidisation of aromatic isocyanates, in particular phospholines or phospholine oxides. The phospholines or phospholidines stated in U.S. Pat. No. 2,853,518 and in particular the phospholine oxides stated in U.S. Pat. No. 2,853,473 are, for example, suitable, wherein 1-methyl-1-oxo-phospholene is particularly preferred according to the invention. The catalysts are generally used in a quantity of 50 to 1000 ppm (weight) related to the weight of the starting isocyanate when the process according to the invention is performed. The catalyst may be incorporated into the starting isocyanate at the beginning of the reaction or also partly in portions during the reaction. The stated quantity refers to the entire quantity of catalyst used.

To perform the process according to invention, in a first stage the starting isocyanate containing the catalyst, optionally with the addition of further quantities of catalyst in portions, is heated to the reaction temperature of 120 to 220, preferably 160° to 180° C. until a maximum of 80, preferably 50 to 70% of the isocyanate groups of the starting isocyanate have been consumed by carbodiimidisation, which may readily be ascertained by the quantity of carbon dioxide eliminated. During this first stage of the process, the pressure conditions are adjusted such that the starting isocyanate is not distilled off. To this end, it is generally sufficient to operate under standard pressure. The reaction preferably proceeds continuously, for example in a series of stirred-tank reactors.

The second stage of the process according to the invention consists of removing the unreacted monoisocyanate together with the catalyst from the reaction mixture by distillation. The essential feature of the invention is that the unreacted starting isocyanate being distilled off in this stage acts as an entraining agent for the catalyst. This removal of the starting isocyanate and catalyst by distillation generally proceeds within the temperature range from 150° to 220° C. at an operating pressure of 1 to 50 mbar in a continuously operated distillation plant, for example in a packed column, wherein it must be ensured that the dwell time of the reaction mixture containing the catalyst in the bottom is as short as possible. No disruption of distillation is observed at dwell times of the order of minutes.

The distillate produced in the second stage of the reaction is a mixture of the starting isocyanate and catalyst, which may be returned to the beginning of the process. The crude product of the process arising as bottom product may, if desired, be subjected to a precision distillation, wherein higher boiling impurities are removed from the carbodiimide distillate. This purification of the product of the process by distillation preferably proceeds continuously using a film evaporator within the temperature range from 150 to 250° C. and within a pressure range of 0.5 to 50 mbar. Colourless carbodiimides are here obtained as distillate with a phosphorus content of below 5 ppm (weight). The products of the process according to the invention are valuable hydrolysis stabilisers for plastics with ester groups.

The following examples further illustrate the process according to the invention.

EXAMPLE 1

1st stage of process:
Partial carbodiimidisation of 2,6-diisopropylphenyl isocyanate 15 kg of 2,6-diisopropylphenyl isocyanate and 0.0028 kg of 1-methyl-1-oxo-phospholene are fed hourly using metering pumps into a continuously operated series of reactors, consisting of 4 stirred reactors each with a capacity of 15 l. The reaction temperature is 175° C., the average dwell time 4 hours. On leaving the series of reactors, the hot mixture of 2,2',6,6'-tetraisopropyl-diphenyl carbodiimide, 2,6-diisopropylphenyl isocyanate and 1-methyl-1-oxo-phospholene is cooled to room temperature. While the isocyanate group content of pure 2,6-diisopropylphenyl isocyanate is 20.7%, the reaction mixture has an NCO content of 7.1%. The reaction mixture therefore contains 34.3 wt.% 2,6-diisopropylphenyl isocyanate and 65.7 wt.% carbodiimide.

2nd stage of the process:
Separation of educt and catalyst by distillation

At an operating pressure of 0.3 mbar at the top of the column, 14 kg per hour of mixture preheated to 105° C. are introduced between the second and third stages of a three-stage distillation column (length of each stage 500 mm, internal diameter 80 mm with SULZER BX woven packing). With a column bottom volume of 2.06 l, the average bottom dwell time is 8.8 minutes. 8 kg per hour of carbodiimide are drained from the bottom and 6 kg per hour of distillate produced, which contains the catalyst 1-methyl-1-oxo-phospholene.

3rd stage of process:
Further preparation of carbodiimide by distillation 22 kg per hour of crude carbodiimide from stage 2 of the process are fed into a film evaporator (O 160 mm, area of heating surface 1.5 m$^2$) at an operating temperature of 180° C. and an operating pressure of 0.9 mbar. The head product obtained is 21.5 kg per hour of ultra-pure 2,2',6,6'-tetraisopropyldiphenyl carbodiimide with a carbodiimide content of 10.8% and an APHA colour value of 230. Phosphorus content is below 5 ppm (weight).

EXAMPLE 2

1180.6 kg of 2,6-diisopropylphenyl isocyanate and 0.5 kg of 1-methyl-1-oxo-phospholene are gradually heated to 165° C. in a stirred reactor with a volume of 2000 l. By means of a gas meter in the waste gas outlet of the reactor, the quantity of carbon dioxide formed as an accompanying product of the carbodiimidisation process may be ascertained. After elimination of 41.1 m$^3$ of $CO_2$ (at standard temperature and pressure), i.e. after approximately 48 hours, the carbodiimidisation process is arrested by cooling the contents of the reactor. The isocyanate group content of the reaction mixture is 8.2%, and the proportion of unreacted 2,6-diisopropylphenyl isocyanate therefore 39.6 wt.%.

Distillation (2nd stage of the process) and purification of the product of the process by distillation (3rd stage of the process) were performed in a manner analogous to example 1. A practically colourless carbodiimide is produced with a phosphorus content of below 3 ppm.

We claim:

1. In a process for the production of aromatic carbodiimides by carbodiimidisation of aromatic monoisocyanates in the presence of organic phosphorus compounds which accelerate the carbodiimidisation of isocyanates with the elimination of carbon dioxide as catalysts at 120° to 220° C., wherein the improvement comprises carrying out the carbodiimidisation in the presence of a distillable phospholine or phospholine oxide catalyst, and removing, at a degree of carbodiimidisation of the monoisocyanates used as starting material of a maximum of 80%, the unreacted starting isocyanate from the reaction mixture by distillation together with the catalyst and isolating the carbodiimide as the distillation residue of said distillation.

2. Process according to claim 1, characterised in that the mixture of starting isocyanate and catalyst isolated as the distillate is returned to the carbodiimidisation process.

3. Process according to claim 1, characterised in that the product of the process obtained as a distillation residue is purified by distillation.

4. Process according to claims 1, characterised in that 2- and/or 6-alkyl-substituted phenyl isocyanate is used as the starting isocyanate.

5. Process according to claims 1, characterised in that 2,6-diisopropylphenyl isocyanate is used as the starting isocyanate.

6. Process according to claims 1, characterised in that 1-methyl-1-oxo-phospholene is used as the catalyst.

* * * * *